United States Patent [19]

Goldstein et al.

[11] Patent Number: 4,543,340
[45] Date of Patent: Sep. 24, 1985

[54] RADIOIMMUNOASSAY OF THYMOSIN $\beta_4$

[75] Inventors: Allan L. Goldstein, Washington, D.C.; Teresa L. K. Low, Annandale, Va.; John McClure, Houston, Tex.; Paul H. Naylor, Bowie, Md.

[73] Assignee: George Washington University, Washington, D.C.

[21] Appl. No.: 482,384

[22] Filed: Apr. 7, 1983

[51] Int. Cl.⁴ .................. G01N 33/56; A61K 39/00; C07G 7/00; C07C 103/52
[52] U.S. Cl. ................ 436/542; 260/112 R; 260/112.5 R; 424/85; 436/543; 436/545; 436/804; 436/815
[58] Field of Search ............. 436/500, 536, 538–542, 436/543–545, 547, 804, 815, 817; 260/112 R, 112.5 R; 424/177, 85

[56] References Cited

U.S. PATENT DOCUMENTS

| | | | |
|---|---|---|---|
| 4,079,127 | 3/1978 | Goldstein et al. | 424/177 |
| 4,264,571 | 4/1981 | Goldstein et al. | 436/542 |
| 4,297,276 | 10/1981 | Goldstein et al. | 260/112.5 R |
| 4,339,427 | 7/1982 | Goldstein et al. | 260/112 R |
| 4,388,234 | 6/1983 | Horecker | 260/112.5 R |
| 4,395,404 | 7/1983 | Low et al. | 424/177 |
| 4,427,783 | 1/1984 | Newman et al. | 436/542 |

OTHER PUBLICATIONS

Filipowicz et al., Proc. Natl. Acad. Sci. USA, 80:1811–1815, (1983).
Low et al., Proc. Natl. Acad. Sci. USA, 78:1162–1166, (1981).
Hannappel et al., Proc. Natl. Acad. Sci. USA, 79:2172–2175, (1982).
Goodall et al., Arch. Biochem. Biophys., 221:598–601 (3/1983).
Low et al., J. Biol. Chem., 257:1000–1006, (1982).
Xu et al., Proc. Natl. Acad. Sci. USA, 79:4006–4009, (1982).
Chen et al., Proc. Natl. Acad. Sci. USA, 80:5980–5984, (1983).
Hannappel et al., Biochem. Biophys. Res. Comm., 104:266–271, (1982).
Goodall et al., J. Immunol., 131:821–825, (1983).

Primary Examiner—Christine M. Nucker
Attorney, Agent, or Firm—Jon S. Saxe; Bernard S. Leon; George W. Johnston

[57] ABSTRACT

A radioimmunoassay for the polypeptide thymic hormone thymosin $\beta_4$ is described. The assay employs a radiolabelled Tyr-C13-thymosin $\beta_4$-analogue as probe and a thymosin $\beta_4$ antibody.

14 Claims, No Drawings

RADIOIMMUNOASSAY OF THYMOSIN β4

BACKGROUND OF THE INVENTION

Thymosin β4 is a heat stable, acidic polypeptide composed of 43 amino acid residues. The thymic hormone has been isolated from calf thymus thymosin fraction 5 and its amino acid sequence determined. Thymosin β4 is one of several polypeptides present in thymosin fraction 5 which participates in the regulation, differentiation and function of thymic dependent lymphocytes (T cells). The isolation, characterization and use of thymosin β4 is described in greater detail in U.S. Pat. No. 4,297,276.

An immunoassay for a polypeptide hormone of the thymus known as thymopoietin or thymin is disclosed in U.S. Pat. No. 4,055,633. In particular, this patent discloses a radioimmunoassay for thymopoietin utilizing an antibody elicited by an immunogen comprising purified thymopoietin covalently coupled to an immunogenic carrier material such as bovine gamma globulin using glutaraldehyde as the coupling agent. The labelled antigen used in the assay is preferably $^{125}$I-thymopoietin.

It should be noted that thymopoietin is totally non-analogous to thymosin β4 in structure, amino acid composition and sequence, biological activity profile, physical properties and immunological properties.

A radioimmunoassay for a partially purified thymosin fraction, i.e. thymosin fraction 5, which is now known to contain a mixture of a number of polypeptides, is reported by Schulof et al., Fed. Proc. 32,962 (1973). See also Goldstein et al., Fed. Proc. 33,2053 (1974).

U.S. Pat. No. 4,264,571 describes a radioimmunoassay for thymosin α1. This assay employs an antibody elicited by an immunogen comprising thymosin α1 covalently linked to hemocyanin by a glutaraldehyde linking group. $^{125}$I-thymosin α1 was used as the label and was prepared by treatment with Bolton-Hunter reagent. The assay procedure utilized the double antibody method to achieve precipitation of the immune complex. Goat anti-rabbit gamma globulin was used as the second antibody.

U.S. Pat. No. 4,339,427 describes an improved radioimmunoassay for thymosin α1 using synthetic thymosin α1 to raise the antibody and an analogue of thymosin α1, (Tyr$^1$)-thymosin α1 as the peptide to be labelled.

DESCRIPTION OF INVENTION

The present invention relates to a radioimmunoassay for measuring thymosin β4.

Thymosin β4 is a heat stable acid polypeptide thymic hormone composed of 43 amino acids having the following amino acid sequence:

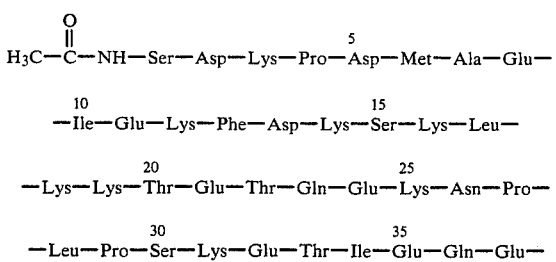
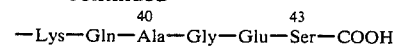

The immunogen utilized to prepare the antibody for the assay is readily obtained by covalently bonding thymosin β4 to a conventional immunological carrier material. The source of the thymosin β4 is not narrowly critical to the practice of the invention. Suitable thymosin β4 can be derived from fraction 5 obtained from various mammalian sources. Thus, for example, thymosin β4 obtained from human, bovine, sheep or porcine fraction 5 preparations can be employed. This is possible due to the homology of amino acid sequences of thymosin β4 derived from these various mammalian species.

Alternatively and preferably, thymosin β4 obtained by peptide synthesis procedures now known in the art can be employed. Thus, for example, thymosin β4 produced by solid phase or solution phase procedures can be suitably employed.

As used herein the term "immunogenic carrier material" is meant to include those materials which have the property of independently eliciting an immunogenic response in a host animal and which can be covalently coupled to thymosin β4 either directly via the formation of peptide or ester bonds between free carboxyl, amino or hydroxyl groups in thymosin β4 and corresponding groups on the immunogenic carrier material or alternatively by bonding through a conventional bifunctional linking group.

The covalent coupling of thymosin β4 to the immunogenic carrier material can be carried out in a manner well known in the art. Thus, for example, for direct covalent coupling it is possible to utilize a carbodiimide, preferably dicyclohexylcarbodiimide or 1-ethyl-3-(3-dimethylaminopropyl)carbodiimide as coupling agent. In such direct coupling it is desirable to utilize a slightly acidic reaction medium for this step, e.g., a medium having a pH in the range of from about 3 to 6.5, most preferably in the range of from about 4 to 6.5.

A suitable bifunctional linking group for effective coupling is a C$_{2-7}$ dialkanal such as glutaraldehyde. Such coupling in this alternate embodiment can conveniently be carried out using the conditions described by Avrameas, Immunochemistry 6, 43 (1969).

The resulting immunogen can be utilized without further purification or, although not necessary, after dialysis to remove any unreacted thymosin β4 and coupling reagents.

Suitable immunogenic carrier materials which can be used in the preparation of the immunogens of the instant invention include proteins; natural or synthetic polymeric compounds such as polypeptides, e.g., polylysine or copolymers of amino acids; polysaccharides; and the like. Particularly preferred carrier materials are proteins and polypeptides, especially proteins.

The identity of the protein used as an immunogenic carrier material in the preparation of an immunogen of the instant invention is not critical. Examples of suitable proteins include mammalian serum proteins such as, for example, human gamma globulin, human serum albumin, bovine serum albumin, methylated bovine serum albumin, rabbit serum albumin, bovine gamma globulin and equine gamma globulin or non-mammalian proteins such as hemocyanin, particularly Keyhole Limpet hemocyanin (KLH). Other suitable proteins will be known to one skilled in the art.

The immunogen of the present invention may be utilized to induce formation of antibodies specific to thymosin $\beta_4$ in host animals by injecting the immunogen in such a host, preferably using an adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with thymosin $\beta_4$. Due to a high level of homology between the thymosin $\beta_4$ sequences derived from various mammalian species, it is possible to utilize antibodies raised against one species of thymosin $\beta_4$ to assay for thymosin $\beta_4$ of other mammalian species.

Tyr-C13-thymosin $\beta_4$ is used as the substrate for radioiodination. The expression Tyr-C13-thymosin $\beta_4$ refers to a polypeptide consisting of the 13 C-terminal amino acids of thymosin $\beta_4$ with tyrosine attached at the N-terminal end Tyr-C13-thymosin $\beta_4$ has the following amino acid sequence:

Tyr-Lys-Glu-Thr-Ile-Glu-Gln-Glu-Lys-Gln-Ala-Gly-Glu-Ser-COOH.

The use of this analogue represents a distinct improvement over methods employing the whole molecule, since they require either the use of Bolton-Hunter radiolabelling or chemical modification with non-labelled Bolton-Hunter reagent followed by classical radiolabelling techniques. The analogue provides a labelled product of high specific acitivity which retains a high degree of immunoreactivity. The tyrosine residue incorporated into the sequence at the amino-terminal end of the peptide presents less steric hindrance to binding with antibody than would be attained with the addition of the aromatic ring structure at sites internal and perhaps near to the antigenic determinant. Additionally, it has been found that the Tyr-C13-thymosin $\beta_4$ can be labelled more uniformly and reproducibly than can the natural thymosin $\beta_4$ with Bolton-Hunter reagent. The use of chemically synthesized peptides in the assay is preferred. It gives the assay a high degree of specificity since there is no possibility of contamination of the preparation with compounds which could co-purify from the tissue of origin. Tyr-C13-thymosin $\beta_4$, which is used as the substrate for radioiodination, can be conveniently prepared using known solid phase peptide synthesis procedures in the same manner as one would prepare thymosin $\beta_4$ with the exception that only the 13 carboxyterminal amino acids of thymosin $\beta_4$ are synthesized and the last amino acid added is tyrosine.

While radioiodinated Tyr-C13-thymosin $\beta_4$ is the reagent of preference in the radioimmunoassay, it is possible to employ other radiolabelled reagents such as (Tyr$^1$)-thymosin $\beta_4$ or (Tyr$^1$)-desacetyl thymosin $\beta_4$ which can be labelled with iodine $^{125}$I or carbon 14 ($^{14}$C). (Tyr$^1$)-thymosin $\beta_4$ has the following amino acid sequence:

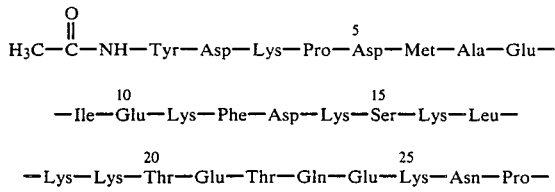

$$-\text{Leu}-\text{Pro}-\text{Ser}-\text{Lys}-\text{Glu}-\text{Thr}-\text{Ile}-\text{Glu}-\text{Gln}-\text{Glu}-$$

$$-\text{Lys}-\text{Gln}-\text{Ala}-\text{Gly}-\text{Glu}-\text{Ser}-\text{COOH}$$

(Tyr$^1$)-desacetyl thymosin $\beta_4$ has the following amino acid sequence:

$$\text{Tyr}-\text{Asp}-\text{Lys}-\text{Pro}-\text{Asp}-\text{Met}-\text{Ala}-\text{Glu}-\text{Ile}-\text{Glu}-$$

$$-\text{Lys}-\text{Phe}-\text{Asp}-\text{Lys}-\text{Ser}-\text{Lys}-\text{Leu}-\text{Lys}-\text{Lys}-\text{Thr}-$$

$$-\text{Glu}-\text{Thr}-\text{Gln}-\text{Glu}-\text{Lys}-\text{Asn}-\text{Pro}-\text{Leu}-\text{Pro}-\text{Ser}-$$

$$-\text{Lys}-\text{Glu}-\text{Thr}-\text{Ile}-\text{Glu}-\text{Gln}-\text{Glu}-\text{Lys}-\text{Gln}-\text{Ala}-$$

$$-\text{Gly}-\text{Glu}-\text{Ser}-\text{COOH}$$

Tritium can be introduced into such reagents by use of isotopic exchange procedures known in the art. The production of $^{14}$C-(Tyr)C13-thymosin $\beta_4$ or $^{14}$C-(Tyr$^1$)-desacetyl-thymosin $\beta_4$ or $^{14}$C-(Tyr$^1$)-thymosin $\beta_4$ is readily accomplished by incorporating one or more commercially available $^{14}$C-labelled amino acids into the appropriate steps of the solid phase synthesis procedures.

Various assay methods can be employed in the practice of this invention. In one such procedure, known amounts of a sample to be assayed, the thymosin $\beta_4$ specific antibody and the labelled thymosin $\beta_4$ are mixed together and allowed to stand. The antibody antigen complex is separated from the unbound reagents by procedures known in the art, i.e., by treatment with ammonium sulfate, polyethylene glycol, second antibody either in excess or bound to an insoluble support, dextran coated charcoal and the like. The concentration of labelled thymosin $\beta_4$ or thymosin $\beta_4$ fragment is determined in either the bound or unbound phase and the thymosin $\beta_4$ content of the sample can then be determined in either the bound or unbound phase by comparing the level of labelled component observed to a standard curve in a manner known per se. A suitable standard curve can be obtained by mixing known amounts of thymosin $\beta_4$ with fixed amounts of labelled thymosin $\beta_4$ and the thymosin $\beta_4$ specific antibody and determining the degree of binding for each such known amount.

If desired, the antibody can be treated with various natural materials to increase specificity. A suitable treating agent is thymosin fraction 5 derived from any mammalian organ which does not contain thymosin $\beta_4$ producing cells. Suitable organs include kidney, liver and brain. Mammalian sources for such organs include camel, sheep, horses, monkey, pig, human and the like.

The present invention is further illustrated by the following examples. As used herein "Boc" indicates the protecting group t-butyloxycarbonyl; "Bzl" indicates the protecting group benzyloxycarbonyl; and "2-CIZ" indicates the protecting group 2-chlorobenzyloxycarbonyl.

EXAMPLE 1

Preparation of Tyr-C13-thymosin $\beta_4$;

Tyr-Lys-Glu-Thr-Ile-Glu-Gln-Glu-Lys-Gln-Ala-Gly-Glu-Ser

Boc-Ser(Bzl)-OCH$_2$-C$_6$H$_4$-Resin (2.5 g; 1.0 mmol) was placed in a peptide synthesis vessel and the solid phase synthesis carried out with the following steps in each cycle: (1) three washings with CH$_2$Cl$_2$, (2) prewash with 40% trifluoroacetic acid (TFA) in CH$_2$Cl$_2$, (3) stir 28 min. with 40% TFA in CH$_2$Cl$_2$, (4) three washings with CH$_2$Cl$_2$, (5) prewash with 10% triethylamine (Et$_3$N) in CH$_2$Cl$_2$, (6) stir 8 min. with 10% Et$_3$N in CH$_2$Cl$_2$, (7) three washings with CH$_2$Cl$_2$, (8) stir 120 min. with Boc-Glu(OBzl)-OH (3 mmol; 1.01 g) and dicyclohexylcarbodiimide (DCC) (3 mmol; 0.62 g), (9) three washings each with CH$_2$Cl$_2$, 50% isopropyl alcohol in CH$_2$Cl$_2$ and then CH$_2$Cl$_2$.

The synthetic cycle was repeated using the following amino acid derivatives, sequentially, in step (8): Boc-Gly-OH, Boc-Ala-OH, Boc-Gln-OH, Boc-Lys(2-CIZ)-OH, Boc-Glu(OBzl)-OH, Boc-Gln-OH, Boc-Glu(OBzl)-OH, Boc-Ile-OH, Boc-Thr(Bzl)-OH, Boc-Glu(OBzl)-OH, Boc-Lys(2-CIZ)-OH, Boc-Tyr(Bzl), and 1-Hydroxybenzotriazole (HOBT, 6 mmol; 0.81 g) was added to each coupling reaction involving Boc-Gln-OH in step (8). On completion of the synthesis, 4.14 g of protected peptide resin was obtained. It was then subjected to HF cleavage (100 ml anhydrous HF, 10 ml anisole) at 0° for 30 min. After removal of excess HF the resin-peptide mixture was extracted with 1% acetic acid and lyophilized to give 1.7 g of crude product in slightly beige colored powder. It was then further purified by high pressure liquid chromatography on a $\mu$Bondapak C18 column (10- um, 0.39 $\times$ 30 cm) at 35° C. The buffer in reservoir A was 0.05% TFA (pH-23) and in reservoir B was acetonitrile containing 0.05% TFA. Peptides were detected by UV absorbance at 210 nm. Flow rate was set at 1.5 ml/min. The peptides were eluted from the column with 5% B for 10 min. followed by a linear gradient 45 to 30% B in 50 min. Tyr-C13-thymosin $\beta_4$ was eluted from the column at 28 min. Amino acid analysis: Glu, 6.09; Thr, 0.85; Ser, 0.86; Gly, 1.08; Ala, 1.12; Ile, 0.90; Tyr, 0.83; Lys, 2.07.

EXAMPLE 2

(a) Preparation of antiserum

Synthetic thymosin $\beta_4$ (entire molecule of 43 residues) was covalently coupled to KLH by means of glutaraldehyde. Synthetic thymosin $\beta_4$ (2.75 mg) and Keyhole Limpet Hemocyanin (KLH, 4.15 mg) were placed in a 12$\times$75 mm stoppered plastic tube with 1.5 ml of 0.25 M sodium phosphate, pH 7.4. Glutaraldehyde was added to a final concentration of 1.25% (w/v) by the addition of 75 $\mu$l of 25% aqueous glutaraldehyde. After gentle agitation of the reaction vessel for 3 hr. at room temperature, the solution was diluted with sterile, physiologic saline (0.15 M sodium chloride) to a concentration of thymosin $\beta_4$ of 50 $\mu$g/ml. The mixture of reaction products was used without purification for immunizations.

New Zealand White rabbits (young adults of 5 to 6 lbs.) were immunized with 50 $\mu$g of synthetic thymosin $\beta_4$ conjugated to KLH at 20–30 intradermal sites on the back of each rabbit, according to the method of Vaitukaitis, et al. (J. Clin. Endo, 33, 988 (1971)). An emulsion, consisting of equal volumes of aqueous protein solution and Freund's complete adjuvant, was prepared in order that each rabbit received the 50 $\mu$g of antigen in 2 ml of emulsion. Booster injections of 50 $\mu$g thymosin $\beta_4$ (as the KLH conjugate) per animal in booster injections were given every two weeks over a four-month period (i.e., a primary immunization followed by eight booster injections). Fourteen days after the eighth booster, the first bleeding was made. Additional boosts at monthly intervals and a final 10 day rest period were permitted before the bleedings that produced antiserum suitable for the immunoassay.

(b) Radioiodination of (Tyr)-C13-thymosin $\beta_4$ analogue

A modification of the chloramine T method of iodination was utilized to radioiodinate the (Tyr)-thymosin $\beta_4$ analogue (Greenwood, F. C., Hunter, W. M. and Glover, J. S., Biochem. J. 89, 114 1963). The $\beta_4$ analogue was brought into solution at a concentration of 166 $\mu$g/ml in 0.5 M phosphate buffer (pH=6.0). To 12 $\mu$l of the analogue (28 g) was added 5 mCi of Na I$^{125}$ in 20 $\mu$l of phosphate buffer. Chloramine T was prepared at 0.5 mg/ml of phosphate buffer and 10 $\mu$l added with mixing. After 90 sec., 100 $\mu$l of metabisulfate (4 nmoles/100 $\mu$l; 7.6 $\mu$g/ml) was added to stop the reaction. To effect an efficient transfer to the G-10 column required for separation of free $^{125}$I and labeled peptide, 50 $\mu$l of normal serum was also added to the reaction tube prior to transfer.

The sephadex G-10 column (0.7$\times$10 cm) was equilibrated with 10% CH$_3$COOH with 0.1% ovalbumin added. One ml aliquots were collected and the labeled peptide peak was used as the tracer. The tracer was aliquoted (5 $\mu$l) and frozen immediately. Prior to assay, tracer was diluted to give 10,000 cpm/50 $\mu$l. Rechromatography of tracer after 4 weeks was possible, extending the usefulness of a single labeling to 6–8 weeks.

(c) Radioimmunoassay Protocol

Stock solution of synthetic thymosin $\beta_4$ at a concentration suitable for the working range of the assay (between 0.5 and 37.5 ng/100 $\mu$l) were prepared in a radioimmunoassay buffer (RIAB) and frozen at $-20°$ C. The RIAB was phosphate buffered saline (pH=7.4, 0.01 M sodium phosphate and 0.15 M NaCl) to which was added 0.05% (wt/volume) NaN$_3$, 0.01 mM EDTA, and (NH$_4$)$_2$SO$_4$-fractionated normal rabbit serum (NRS) at a final dilution of 1/200. The NRS served as both a protein to prevent nonspecific binding of tracer and as a carrier in the double antibody precipitation step. Nine standards containing 0.5 to 37.5 ng/100 $\mu$l were prepared from the stock solutions and frozen at $-70°$ C. for use as needed. Unknown samples required 5–20 $\mu$l of serum per assay and saline was added to give 100 $\mu$l/sample. All tubes were brought to a final volume of 400 $\mu$l with RIAB. A 50 $\mu$l aliquot of stock antiserum (1/200 dilution) was added to each tube. The dilution gives 20–25% binding of tracer and a final dilution of 1/2000. Nonspecific binding was assessed by processing tubes containing all the assay reagents except the specific anti-thymosin $\beta_4$ antiserum. The tubes were vortexed and incubated for 24 hrs. at 4° C. Separation of free from bound tracer was carrier out by the addition of 50 $\mu$l of a goat-anti-rabbit IgG preparation adjusted to give maximum precipitation of tracer. After addition of 2nd antibody and vortexing, the samples were incubated overnight at 4° C. The immunoprecipitate was pelleted by centrifugation at 1500×G for 25 min. at 4° C. The supernatants were aspirated and discarded, and the radioactivity in the immunoprecipitates was measured in an automatic gamma spectrometer. The counts per minute for standards and unknowns ($B_i$) were corrected for nonspecific background, usually 5% of the total radioactivity and divided by the corrected counts per minute for reaction tubes in which no competing antigen was introduced ($B_0$). The data was analyzed on a Beckman system DP-5500 which plots log dose (x axis) vs observed counts and calculates data using the four-parameter logistic method in which the dose-response curve is described by:

$$y = \frac{(A - D)}{1 + (x/C)B} + D$$

where y=response, x=the concentration, A=the response when x=O($B_0$), B=a slope factor, C=the dose corresponding to the response halfway between A and D, D=the response for an infinite concentration. Rodbard D. et al., Radioimmunoassay and Related Procedures in Med., 1, 469 (1978).

(d) Results using the RIA for thymosin $\beta_4$

Synthetic thymosin $\beta_4$ can be measured using antibody and $^{125}I$ Tyr-C13-thymosin $\beta_4$ analogue over a range of 0.4–37.5 ng/tube (FIG. 1). The thymosin $\beta_4$ levels in serum from human, bovine, mouse, hamster and guinea pig were parallel to the standard curve using between 1 and 10 μl. The minimal detectable serum levels were 5 ng/ml and a final antibody concentration of 1/2000 was used to give a 20-25% binding of tracer to antibody.

The initial specificity of the RIA was determined by assaying preparations of several putative thymic hormones and various serum proteins for cross-reactivity (Table 1). In the assay for each preparation increasing amounts of each protein were added to the RIA system until levels were reached that were well above the known physiologic concentrations in blood or until a practical limit, determined by the amount of each preparation available, was reached. For those preparations that did not produce a response significantly different from the zero dose levels, taken to be 20% inhibition, the largest dose tested is indicated. Only synthetic thymosin $\beta_4$ and the Tyr-C13-thymosin $\beta_4$ analogue displaced tracer at levels in the 0.5 ng range. Prealbumin did not cross-react at levels of 100 μg/tube. Thymopoietin and thymosin $\alpha_7$ displaced 20% of the tracer at levels of 10 μg. Thymosin $\alpha_1$ which is present in serum in pg amounts did not cross-react at 100 ng/tube.

TABLE 1

| Specificity of RIA for Thymosin $\beta_4$ | |
|---|---|
| Protein Tested | Amount required to displace at least 20% of $^{125}I$ Tyr-C13-Thymosin $\beta_4$ |
| A. Non-thymic proteins and peptides | |
| Hemocyanin (KLH) | >100 μg |
| Albumin (human) | >100 μg |
| Hemaglobin (human) | >100 μg |
| Myoglobin (equine) | >100 μg |
| Polyasparagine | >100 μg |
| Prolactin | >10 μg |
| Prealbumin | >100 μg |
| B. Thymic Peptides | |
| Thymopoietin II | 10 μg |
| Thymosin $\alpha_7$ | 10 μg |

TABLE 1-continued

| Specificity of RIA for Thymosin $\beta_4$ | |
|---|---|
| Protein Tested | Amount required to displace at least 20% of $^{125}I$ Tyr-C13-Thymosin $\beta_4$ |
| Thymosin $\beta_4$ | 0.1 ng |
| Thymosin $\beta_4$ ($C_{14}$) | 0.1 ng |
| Thymosin $\alpha_1$ | >1 μg |

The levels of circulating thymosin $\beta_4$ in human serum is shown in Table 2. While the intra assay accuracy is within the range expected for such assays, the normal levels vary considerably between individuals.

TABLE 2

| Thymosin $\beta_4$ levels in human serum | | | |
|---|---|---|---|
| Source of Serum | Age (yrs) | Number | Thymosin (ng/ml) |
| male blood | 25–50 | 33 | 850 ± 249* |
| female blood | 25–50 | 23 | 700 ± 168 |
| cord blood | new born | 20 | 1840 ± 154 |

*expressed as mean ± standard deviation

We claim:

1. A polypeptide, Tyr-C13-Thymosin $\beta_4$, having the following amino acid sequence:

Tyr-Lys-Glu-Thr-Ile-Glu-Gln-Glu-Lys-Gln-Ala-Gly-Glu-Ser-COOH.

2. A radioactive tracer useful in assaying for thymosin $\beta_4$ comprising a polypeptide selected from the group consisting of:

(a) Tyr-C13-thymosin $\beta_4$, having the following amino acid sequence:

Tyr-Lys-Glu-Thr-Ile-Glu-Gln-Glu-Lys-Gln-Ala-Gly-Glu-Ser-COOH;

(b) (Tyr$^1$)-desacetyl thymosin $\beta_4$ having the following amino acid sequence:

Tyr—Asp—Lys—Pro—Asp—Met—Ala—Glu—Ile—Glu—
            5                              10
—Lys—Phe—Asp—Lys—Ser—Lys—Leu—Lys—Lys—Thr—
                    15                              20
—Glu—Thr—Gln—Glu—Lys—Asn—Pro—Leu—Pro—Ser—
                    25                              30
—Lys—Glu—Thr—Ile—Glu—Gln—Glu—Lys—Gln—Ala—
                    35                              40
—Gly—Glu—Ser—COOH;
        43 and (c) (Tyr$^1$)-thymosin $\beta_4$ having the following amino acid sequence:

$$H_3C-\overset{O}{\overset{\|}{C}}-NH-Tyr-Asp-Lys-Pro-Asp-Met-Ala-Glu-$$
                                                    5
—Ile—Glu—Lys—Phe—Asp—Lys—Ser—Lys—Leu—
            10                      15
—Lys—Lys—Thr—Glu—Thr—Gln—Glu—Lys—Asn—Pro—
            20                              25
—Leu—Pro—Ser—Lys—Glu—Thr—Ile—Glu—Gln—Glu—
            30                              35

—Lys—Gln—Ala—Gly—Glu—Ser—COOH
            40              43 said polypeptide being bound to or incorporating a radioisotope.

3. The radioactive tracer of claim 2 which is $^{125}$I-(Tyr)C13-thymosin $\beta_4$, having the following amino acid sequence:

$^{125}$I-Tyr-Lys-Glu-Thr-Ile-Glu-Gln-Glu-Lys-Gln-Ala-Gly-Glu-Ser-COOH.

4. An immunogen comprising thymosin $\beta_4$ having the following amino acid sequence:

$$H_3C-\overset{O}{\overset{\|}{C}}-NH-Ser-Asp-Lys-Pro-Asp-Met-Ala-Glu-$$
                                                5

—Ile—Glu—Lys—Phe—Asp—Lys—Ser—Lys—Leu—
   10                          15

—Lys—Lys—Thr—Glu—Thr—Gln—Glu—Lys—Asn—Pro—
    20                          25

—Leu—Pro—Ser—Lys—Glu—Thr—Ile—Glu—Gln—Glu—
    30                          35

—Lys—Gln—Ala—Gly—Glu—Ser—COOH
    40              43 covalently bound to an immunological carrier material.

5. An immunogen as claimed in claim 4, wherein the immunological carrier material is Keyhole limpet hemocyanin.

6. A radioimmunoassay for thymosin $\beta_4$ in a sample which comprises:
(a) incubating the sample with a known amount of radioactive tracer and an antibody which will selectively complex with thymosin $\beta_4$ or said radioactive tracer;
(b) separating the resulting antibody-antigen complex from uncomplexed radioactive tracer;
(c) measuring the degree of binding of the radioactive tracer in said complex; and
(d) determining the amount of thymosin $\beta_4$ present in said sample by comparing the degree of binding to a standard curve;
wherein the thymosin $\beta_4$ polypeptide has the following amino acid sequence:

$$H_3C-\overset{O}{\overset{\|}{C}}-NH-Ser-Asp-Lys-Pro-Asp-Met-Ala-Glu-$$
                                                5

—Ile—Glu—Lys—Phe—Asp—Lys—Ser—Lys—Leu—
   10                          15

—Lys—Lys—Thr—Glu—Thr—Gln—Glu—Lys—Asn—Pro—
    20                          25

—Leu—Pro—Ser—Lys—Glu—Thr—Ile—Glu—Gln—Glu—
    30                          35

—Lys—Gln—Ala—Gly—Glu—Ser—COOH
    40              43 and a radioactive tracer of claim 2.

7. The radioimmunoassay of claim 6, wherein the radioactive tracer is $^{125}$I-(Tyr)-C13-thymosin $\beta_4$ having the following amino acid sequence;

$^{125}$I-Tyr-Lys-Glu-Thr-Ile-Glu-Gln-Glu-Lys-Gln-Ala-Gly-Glu-Ser-COOH.

8. A radioimmunoassay as claimed in claim 7, wherein the antibody is an antibody which is elicited in a mammal in response to an immunogen comprising thymosin $\beta_4$ covalently coupled to an immunological carrier material.

9. A radioimmunoassay as claimed in claim 8, wherein said immunological carier material is Keyhole limpet hemocyanin.

10. An antibody which selectively recognizes and binds the polypeptide thymosin $\beta_4$.

11. An antibody as claimed in claim 10 which is elicited from a host animal which has been injected with an immunogen comprising thymosin $\beta_4$ which is covalently coupled to an immunogenic carrier material.

12. An antibody as claimed in claim 11, wherein said immunogenic carrier material is Keyhole limpet hemocyanin.

13. The polypeptide (Tyr$^1$)-desacetyl thymosin $\beta_4$, having the following amino acid sequence:

Tyr—Asp—Lys—Pro—Asp—Met—Ala—Glu—Ile—Glu—
                5                              10

—Lys—Phe—Asp—Lys—Ser—Lys—Leu—Lys—Lys—Thr—
           15                          20

—Glu—Thr—Gln—Glu—Lys—Asn—Pro—Leu—Pro—Ser—
               25                          30

—Lys—Glu—Thr—Ile—Glu—Gln—Glu—Lys—Gln—Ala—
              35                          40

—Gly—Glu—Ser—COOH
           43

14. The polypeptide (Tyr$^1$)-thymosin $\beta_4$, having the following amino acid sequence:

$$H_3C-\overset{O}{\overset{\|}{C}}-NH-Tyr-Asp-Lys-Pro-Asp-Met-Ala-Glu-$$
                                                5

—Ile—Glu—Lys—Phe—Asp—Lys—Ser—Lys—Leu—
   10                          15

—Lys—Lys—Thr—Glu—Thr—Gln—Glu—Lys—Asn—Pro—
    20                          25

—Leu—Pro—Ser—Lys—Glu—Thr—Ile—Glu—Gln—Glu—
    30                          35

—Lys—Gln—Ala—Gly—Glu—Ser—COOH.
    40              43

* * * * *